United States Patent
Sugai

(10) Patent No.: US 6,458,143 B1
(45) Date of Patent: Oct. 1, 2002

(54) ULTRASONIC TREATMENT INSTRUMENT FOR MEDICAL OPERATION

(75) Inventor: Toshiya Sugai, Tokyo (JP)

(73) Assignee: Olympus Optical Co., Ltd., Tokyo (JP)

( * ) Notice: Subject to any disclaimer, the term of this patent is extended or adjusted under 35 U.S.C. 154(b) by 10 days.

(21) Appl. No.: 09/672,558

(22) Filed: Sep. 28, 2000

(30) Foreign Application Priority Data

Oct. 4, 1999 (JP) .......................................... 11-283153

(51) Int. Cl.[7] ............................................... A61B 17/32
(52) U.S. Cl. ...................................................... 606/169
(58) Field of Search .............................. 606/169, 166, 606/170, 162, 107, 108; 604/22

(56) References Cited

U.S. PATENT DOCUMENTS 4,962,755 A * 10/1990 King et al. ................... 604/22
5,653,724 A * 8/1997 Imonti ......................... 606/169

FOREIGN PATENT DOCUMENTS

EP 0 482 847 4/1992
JP 8-224252 9/1996

* cited by examiner

Primary Examiner—Kevin T. Truong
(74) Attorney, Agent, or Firm—Frishauf, Holtz, Goodman & Chick, P.C.

(57) ABSTRACT

An ultrasonic treatment instrument for medical operation is provided which includes a handpiece having a cover serving as a grip, and an ultrasonic vibrator provided inside the cover for generating ultrasonic vibration. A vibration transmitting member is connected to the ultrasonic vibrator while extending from the handpiece, for transmitting the ultrasonic vibration generated by the ultrasonic vibrator. And a treatment portion is provided at a distal end of the vibration transmitting member, for treating living body tissues by the ultrasonic vibration transmitted by the vibration transmitting member. The vibration transmitting member extends while bent at a plurality of bent portions so that the treatment portion is positioned on or near an extension of a central axis of the handpiece.

11 Claims, 2 Drawing Sheets

ULTRASONIC TREATMENT INSTRUMENT FOR MEDICAL OPERATION

CROSS-REFERENCE TO RELATED APPLICATIONS

This application is based upon and claims the benefit of priority from the prior Japanese Patent Application No. 11-283153, filed Oct. 4, 1999, the entire contents of which are incorporated herein by reference.

BACKGROUND OF THE INVENTION

The present invention relates to an ultrasonic treatment instrument for medical operation in use for treatment of human tissues by ultrasonic vibration energy.

As shown in FIG. 3, a conventional ultrasonic treatment instrument 100, which is used for a medical operation under a microscope, comprises a handpiece 106 having an ultrasonic vibrator for generating the ultrasonic vibration inside a cover, a probe 103 for transmitting the ultrasonic vibration generated by the ultrasonic vibrator, and a sheath 102 for covering the probe 103 from the outside. A distal end of the probe 103 protrudes from a distal end of the sheath 102 and is composed of a treatment portion 101 for treating human tissues by the ultrasonic vibration transmitted by the probe 103.

In the conventional ultrasonic treatment instrument 100, generally, the probe 103 or the handpiece 106 is bent for the purpose of preventing interference to the microscope and maintaining the field of view of the microscope. In FIG. 3, the probe 103 is bent at one portion such that a central axis 02 of the probe 103 is at a predetermined angle to a central axis O1 of the handpiece 106 and that the treatment portion 101 is largely eccentric from an extension of the central axis O1 of the handpiece 106.

Jpn. Pat. Appln. KOKAI Publication No. 8-224252 discloses an ultrasonic treatment instrument for medical operation whose probe 103 is bent at two portions so as to maintain a further wider field of view of the microscope. In this case, one of the two bent portions is positioned near the distal end of the probe. EP 0482847A1 also discloses an ultrasonic treatment instrument for medical operation whose probe 103 is bent at two portions.

Incidentally, a treatment instrument in use under observation of the microscope must be designed such that it is possible to delicately handle the treatment instrument without interfering with the microscope at a handpiece side of the treatment instrument or obstructing the field of view of the microscope. Particularly, in the medical fields such as brain surgery, spinal surgery and the like, the treatment instrument needs to be led to a diseased part through a narrow hole generally called a key hole. For this reason, the treatment instrument used in these fields must be designed such that it is possible to delicately handle the treatment instrument in the key hole without obstructing the field of view of the microscope.

When maintaining the field of view of the microscope and preventing the interference with the microscope are considered only, the treatment instrument only has to have a shape shown in FIG. 3. However, the shape of FIG. 3 is inadequate, in order to delicately handle the treatment instrument as the surgeon expects and, particularly, to allow the treatment instrument to access a diseased part through a narrow hole called a key hole.

That is, the treatment portion 101 of the ultrasonic treatment instrument 100 shown in FIG. 3 is largely eccentric from the extension of the central axis O1 of the handpiece 106. Therefore, it is possible to avoid the interference with the microscope (or other treatment instruments) without obstructing the field of view of the microscope, but difficult to delicately handle the treatment instrument without considering the degree of bending of the probe 103. For example, when the surgeon applies the force along the central axis O1 of the handpiece 106 without considering the degree of bending of the probe 103, he is willing to push the distal end of the probe 103 in the central axis O1. In fact, however, as the direction in which the surgeon applies the force almost unconsciously is not equal to the moving direction of the treatment portion 101 at the distal end of the probe 103 due to the above-explained eccentricity of the treatment portion 101, the distal end of the probe 103 moves in a direction which the surgeon does not expect. This gives very strange feeling to the surgeon and prevents him from delicately handling the treatment instrument.

Similarly to a case where writing a small and beautiful character with a bent writing instrument is not easy, it is difficult to delicately handle the conventional ultrasonic treatment instrument shown in FIG. 3 without considering the degree of bending of the probe 103 thereof. In addition, as various treatment instruments are utilized for the respective purposes in a long-time operation, the surgeon must have a big burden in using the ultrasonic treatment instruments while considering the degree of bending.

As for the ultrasonic treatment instruments disclosed in Jpn. Pat. Appln. KOKAI Publication No. 8-224252 and EP 0482847A1, the same problem as the above-described one occurs as the treatment portion 101 is largely eccentric from the extension of the central axis 01 of the handpiece 106. Particularly, in the treatment instrument of Jpn. Pat. Appln. KOKAI Publication No. 8-224252, one of two bent portions is positioned in the vicinity of the distal end of the probe, i.e. the vicinity of the treatment portion is bent. Therefore, it is inconvenient to handle the treatment instrument in the narrow key hole and the treatment instrument may interfere with other treatment instruments that are simultaneously used. The treatment instrument of EP 0482847A1 also has two bent portions as the distal end of the probe and, therefore, insertion into the key hole is substantially impossible and the treatment instrument cannot be used under a microscope.

BRIEF SUMMARY OF THE INVENTION

The object of the present invention is to provide an ultrasonic treatment instrument for medical operation which, even when used together with a microscope, does not obstruct the field of view of the microscope, and which can prevent interference with the microscope or other treatment instruments and can be delicately handled without causing an uncomfortable feeling.

The object of the present invention can be achieved by an ultrasonic treatment instrument described below. That is, an ultrasonic treatment instrument for medical operation according to the present invention comprises a handpiece having a cover serving as a grip, and an ultrasonic vibrator provided inside the cover for generating ultrasonic vibration, a vibration transmitting member connected to the ultrasonic vibrator while extending from the handpiece, for transmitting the ultrasonic vibration generated by the ultrasonic vibrator, and a treatment portion provided at a distal end of the vibration transmitting member, for treating living body tissues by the ultrasonic vibration transmitted by the vibration transmitting member. The vibration transmitting member extends while bent at a plurality of bent portions so that the treatment portion is positioned on or near an extension of a central axis of the handpiece.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

An embodiment of the present invention will be explained below with reference to the drawings.

Figure 1:
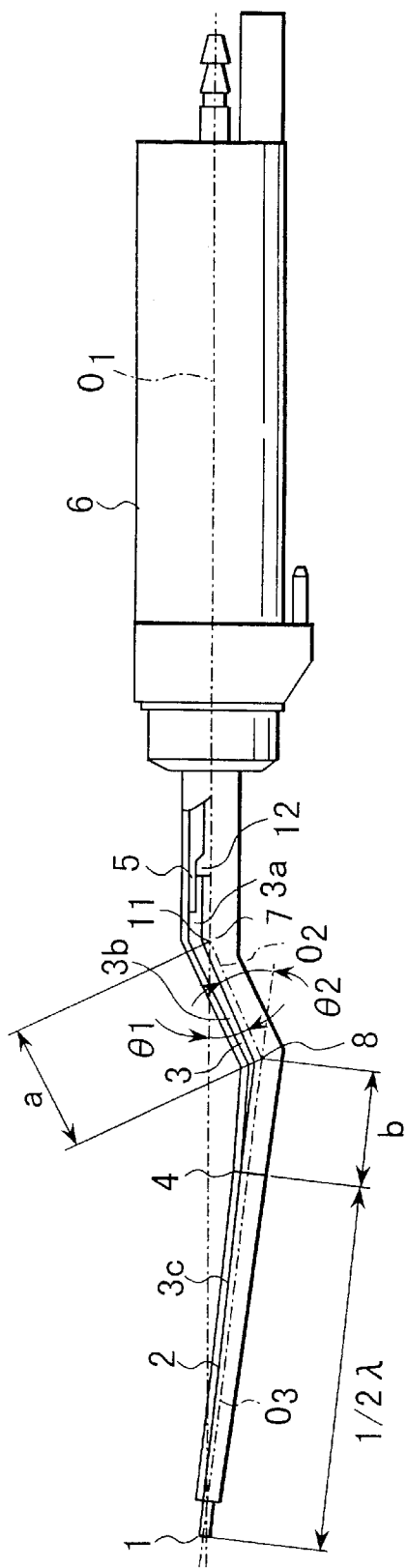
FIG. 1 is a side view of an ultrasonic treatment instrument for medical operation according to an embodiment of the present invention.
Figure 3:
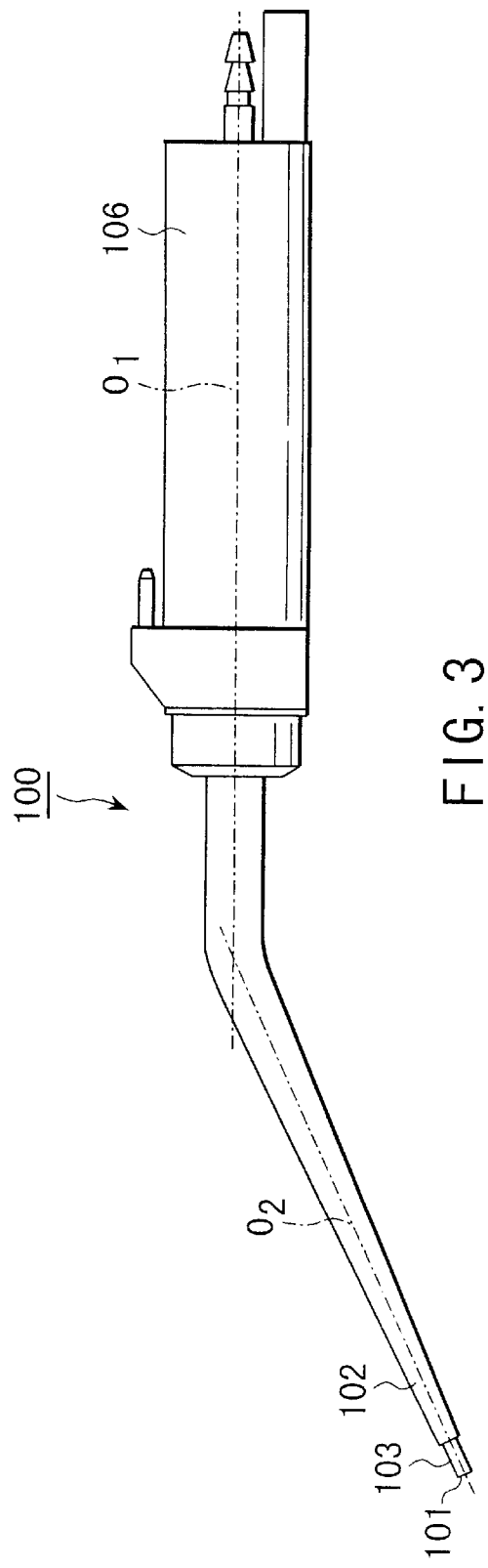
FIG. 3 is a side view of a conventional ultrasonic treatment instrument for medical operation.

The ultrasonic treatment instrument for medical operation according to the present invention, as shown in FIG. 1, is in use for crushing, emulsification, aspiration, coagulation and incision for human tissues. The ultrasonic treatment instrument comprises a handpiece 6 having an ultrasonic vibrator for generating ultrasonic vibration inside a cover composed of a grip, and a probe 3 which is connected to the ultrasonic vibrator and extended from the handpiece 6 and which serves as a vibration transmitting member for transmitting the ultrasonic vibration generated by the ultrasonic vibrator.

In this case, the probe 3 is connected to the ultrasonic vibrator via a horn. The horn and the probe 3 are connected to one another at a connection portion 5 by the mechanical bonding such as engagement or the like.

To prevent the probe 3 from contacting a living body with carelessness, the ultrasonic treatment instrument also comprises a sheath 2 for covering the probe 3 from the outside. The distal end of the probe 3 protrudes from the distal end of the sheath 2 and is composed of a treatment portion 1, which treats human tissues by the ultrasonic vibration transmitted by the probe 3. The probe 3 extends while being bent at two portions (i.e. bent portions 7 and 8) so that the treatment portion 1 is positioned on an extension of a central axis O1 of the handpiece 6 (as described later).

The sheath 2, composed of an elastic or flexible material such as resin or the like, is formed in accordance with the bent shape of the probe 3 so that the sheath 2 can be covered from the distal end thereof after the probe 3 is connected to the handpiece 6. Cooling water is supplied through an annular flow path between the sheath 2 and the probe 3 by cooling water supplying means (not shown). In this case, the supplied cooling water passes through a suction path 12 and is sucked and collected together with human tissues by suction means (not shown).

The probe 3 has a proximal end portion 3a connected to the horn at a connection portion 5, an intermediate portion 3b connected to the proximal portion 3a via the first bent portion 7 of the proximal side, and a distal end portion 3c connected to the intermediate portion 3b via the second bent portion 8 of the distal side. The proximal end portion 3a extends straight, substantially coaxially with the central axis O1 of the handpiece 6. The intermediate portion 3b extends straight such that a central axis O2 thereof is at predetermined angle θ1 with the central axis O1 of the handpiece 6. The distal end portion 3c extends straight such that the treatment portion 1 is positioned on the extension of the central axis O1 of the handpiece 6. A central axis 3 of the distal end portion 3c is at predetermined angle θ2 with the central axis O2 of the intermediate portion 3b. That is, the probe 3 has two bent portions 7 and 8, allows the treatment portion 1 to be positioned on the central axis O1 and is in what is called a bayonet shape.

The first bent portion 7 of the proximal side is positioned in the vicinity of an antinode 11 of the ultrasonic vibration transmitted by the probe 3. The second bent portion 8 of the distal side is remote from the antinode 11 of the ultrasonic vibration by distance a and from a node 4 thereof by distance b. In this case, a and b are set such that a<b or a<<b.

In the embodiment, the probe 3 is set to have a length of one wavelength of the ultrasonic vibration transmitted by the probe 3. Of course, it may be set to have a length of two wavelengths. The entire length of the probe 3 is not particularly limited. It is beneficial to set the effective length and vibration mode in accordance with predetermined frequency and necessary effective length.

If the frequency having the positions of the antinode 11 and the node 4 predetermined in the present invention is a referential frequency, a frequency obtained by multiplying the frequency by an integer can be used. In this case, however, as the wavelength is shorter and the number of nodes 4 increases, the lengths a and b need to be determined such that the first bent portion 7 of the proximal side and the second bent portion 8 of the distal side cannot be close to the node 4.

Figure 2:
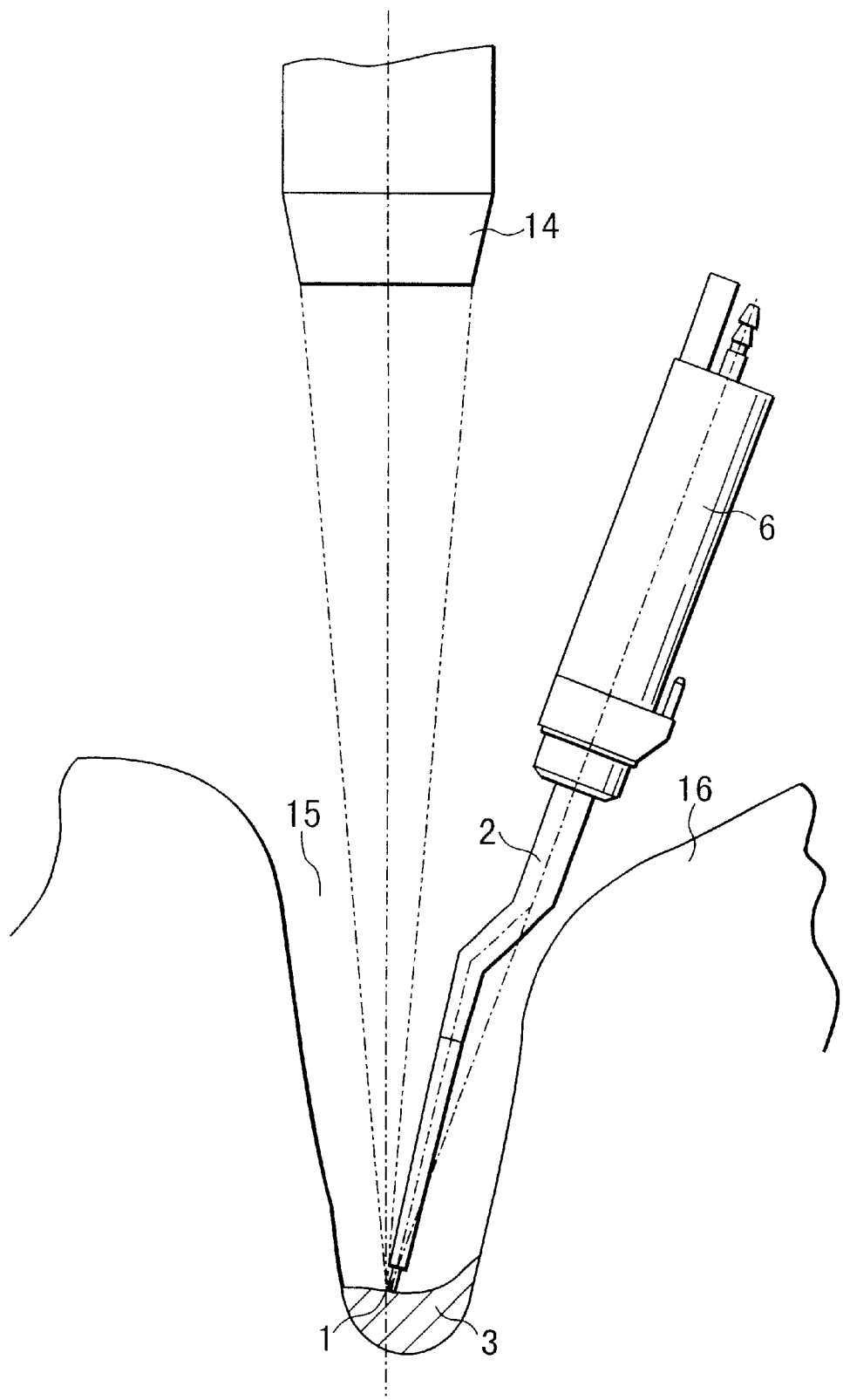
FIG. 2 is a side view explaining the use of the ultrasonic treatment instrument of FIG. 1.

Next, a function of the above-constituted ultrasonic treatment instrument will be explained with reference to FIG. 2.

For example, when a brain tumor 13 is to be removed by using the above-constituted ultrasonic treatment instrument, a tissue 16 is opened through a very narrow key hole 15, and the probe 3 (sheath 2) is inserted into the key hole 15 while observing the tissue 16 by a microscope 14. At this time, the bayonet shape of the probe 3 (sheath 2) allows the probe 3 (sheath 2) to be inserted into the key hole 15 without obstructing the field of view of the microscope 14 or interfering with the microscope 14. As the treatment portion 1 is not bent, handling in the narrow key hole 15 is preferable, and the treatment portion 1 can reach the tumor 13 without interfering with the other treatment instruments. In addition, as the treatment portion 1 is positioned on the extension of the central axis O1 of the handpiece 6, the probe 3 (sheath 2) can be delicately handled without causing an uncomfortable feeling.

As explained above, in the ultrasonic treatment instrument of this embodiment, the probe 3 extends while being bent at a plurality of portions and has a bayonet shape such that the treatment portion 1 is positioned on the extension of the central axis O1 of the handpiece 6. Therefore, even when the ultrasonic treatment instrument is used together with the microscope, interference with the microscope or the other treatment instruments can be prevented. In addition, as the direction in which the surgeon applies the force almost unconsciously is equal to the direction in which the treatment portion 1 at the distal end of the probe 3 moves, the surgeon can delicately handle the ultrasonic treatment instrument without uncomfortable feeling even if he does not especially consider the degree of bending in the probe 3.

Further, the second bent portion 8 of the distal side is remote from the antinode 11 of the ultrasonic vibration by distance a and from the node 4 thereof by distance b and a and b are set such that a<b or a<<b. For this reason, it can be said that the second bent portion 8 is not positioned in the vicinity of the node 4 where the stress is largest, but the antinode 11 where it is smallest. Therefore, it is possible to prevent the stress from concentrating at the bent portion 8.

Generally, the stress becomes larger in proportion to the amplitude obtained at the treatment portion 1 at the distal end of the probe 3. In addition, the materials utilized for the probe 3 respectively have limited stress values. For this reason, if the probe 3 is formed in a shape which allows the concentration of stress to easily occur, the amplitude cannot be largely set as the breakage of the probe 3 needs to be prevented. In the embodiment, however, as the bent portions 7 and 8 where the stress can easily concentrate are positioned remote from the node, it is possible to obtain a large amplitude while preventing the breakage of the probe 3.

In the embodiment shown in FIG. 1, the treatment portion 1 is positioned on the central axis 01 of the handpiece 6, but the invention is not limited to this structure. That is, the treatment portion 1 may also be arranged in the vicinity of the central axis 01 of the handpiece 6 if the arrangement can remove the uncomfortable feeling caused by the bent portions 7 and 8, which the surgeon senses when he uses the ultrasonic treatment instrument.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic treatment instrument for medical operation, comprising:
    a handpiece comprising a cover serving as a grip, and an ultrasonic vibrator which is provided inside the cover and which is adapted to generate ultrasonic vibration;
    a vibration transmitting member having a distal portion positioned on or near a central axis of said handpiece, and comprising a transmitting portion extending from the distal portion along an axis crossing the central axis of said handpiece and a connecting portion connecting a proximal end of said transmitting portion with said ultrasonic vibrator; and
    a treatment portion which is provided at the distal portion of said vibration transmitting member, and which is adapted to treat living body tissues with the ultrasonic vibration transmitted by said vibration transmitting member.

2. An ultrasonic treatment instrument according to claim 1, wherein the treatment portion is directed toward the central axis of the handpiece.

3. An ultrasonic treatment instrument according to claim 1, wherein said vibration transmitting member comprises a plurality of bent portions.

4. An ultrasonic treatment instrument according to claim 3, wherein a distance from each of said plurality of bent portions to an ultrasonic vibration antinode nearest thereto is shorter than a distance from each of said plurality of bent portions to an ultrasonic vibration node nearest thereto, when the ultrasonic vibration is transmitted.

5. An ultrasonic treatment instrument according to claim 4, wherein said plurality of bent portions are provided at or near a part of the vibration transmitting member at which stress is smallest when the ultrasonic vibration is transmitted.

6. An ultrasonic treatment instrument according to claim 4, further comprising a sheath formed of an elastic or flexible material, for covering parts of the vibration transmitting member except for the treatment portion.

7. An ultrasonic treatment instrument according to claim 6, wherein said vibration transmitting member has a bent shape, and said sheath has a shape corresponding to the bent shape of said vibration transmitting member.

8. An ultrasonic treatment instrument for performing at least one of crushing, emulsification, aspiration, coagulation and incision by ultrasonic vibration in a medical operation, said ultrasonic treatment instrument comprising:
    a handpiece having a cover serving as a grip, and an ultrasonic vibrator provided inside the cover for generating ultrasonic vibration; and
    a vibration transmitting member which is mechanically connected to said ultrasonic vibrator, and which is adapted to vibrate at a predetermined frequency in cooperation with said ultrasonic vibrator;
    wherein said vibration transmitting member comprises a plurality of bent portions, an intermediate portion extending toward a central axis of said handpiece along an axis crossing the central axis of said handpiece, and a distal portion arranged on or near the central axis of said handpiece.

9. An ultrasonic treatment instrument for medical operation, comprising:
    a handpiece having a cover serving as a grip, and an ultrasonic vibrator provided inside the cover for generating ultrasonic vibration;
    a vibration transmitting member connected to said ultrasonic vibrator while extending from the handpiece, for transmitting the ultrasonic vibration generated by the ultrasonic vibrator; and
    a treatment portion provided at a distal end of said vibration transmitting member, for treating living body tissues by the ultrasonic vibration transmitted by the vibration transmitting member,
    wherein said vibration transmitting member extends from the handpiece while being bent at a plurality of bent portions such that said treatment portion is directed toward and positioned on or near an extension of a central axis of the handpiece.

10. An ultrasonic treatment instrument for medical operation, comprising:
- a handpiece having a cover serving as a grip, and an ultrasonic vibrator provided inside the cover for generating ultrasonic vibration;
- a vibration transmitting member connected to said ultrasonic vibrator while extending from the handpiece, for transmitting the ultrasonic vibration generated by the ultrasonic vibrator;
- a treatment portion provided at a distal end of said vibration transmitting member, for treating living body tissues by the ultrasonic vibration transmitted by the vibration transmitting member; and
- a sheath formed of an elastic or flexible material, for covering parts of the vibration transmitting member except the treatment portion, wherein said vibration transmitting member extends from the handpiece while being bent at a plurality of bent portions such that said treatment portion is positioned on or near an extension of a central axis of the handpiece.

11. An ultrasonic treatment instrument according to claim 10, wherein said sheath has a shape corresponding to the bending shape of said vibration transmitting member.

* * * * *